United States Patent
Neubardt (10) Patent No.: US 9,636,232 B2
(45) Date of Patent: May 2, 2017

(54) HARVESTING BONE GRAFT MATERIAL FOR USE IN SPINAL AND OTHER BONE FUSION SURGERIES

(71) Applicant: Seth L. Neubardt, Mamaroneck, NY (US)

(72) Inventor: Seth L. Neubardt, Mamaroneck, NY (US)

( * ) Notice: Subject to any disclaimer, the term of this patent is extended or adjusted under 35 U.S.C. 154(b) by 48 days.

(21) Appl. No.: 14/688,544

(22) Filed: Apr. 16, 2015

(65) Prior Publication Data

US 2016/0113780 A1    Apr. 28, 2016

Related U.S. Application Data

(63) Continuation-in-part of application No. 14/524,044, filed on Oct. 27, 2014.

(51) Int. Cl.
*A61B 17/16* (2006.01)
*A61F 2/44* (2006.01)
*A61B 17/32* (2006.01)

(52) U.S. Cl.
CPC ........ *A61F 2/4455* (2013.01); *A61B 17/1635* (2013.01); *A61B 17/1671* (2013.01); *A61B 17/320068* (2013.01); *A61B 2017/320072* (2013.01)

(58) Field of Classification Search
CPC ............ A61B 17/1635; A61B 17/1671; A61B 17/320068; A61B 17/1637; A61B 17/1642; A61F 2/4455; A61F 2/46
See application file for complete search history.

(56) References Cited

U.S. PATENT DOCUMENTS

| | | |
|---|---|---|
| 5,499,985 A | 3/1996 | Hein et al. |
| 6,682,544 B2 | 1/2004 | Mastri et al. |
| 7,201,775 B2 | 4/2007 | Gorensek et al. |
| 7,618,423 B1 | 11/2009 | Valentine et al. |
| 7,972,364 B2 | 7/2011 | Biedermann et al. |
| 8,328,870 B2 | 12/2012 | Patel et al. |
| 8,343,178 B2 | 1/2013 | Novak et al. |
| 8,353,912 B2 | 1/2013 | Darian et al. |
| 8,425,610 B2 | 4/2013 | Guyer et al. |

(Continued)

OTHER PUBLICATIONS

Alphatec Spine, Inc., Solus(R) Anterior Lumbar Interbody Fusion, online advertisement (undated).

(Continued)

*Primary Examiner* — Samuel Hanna
(74) *Attorney, Agent, or Firm* — Law Office of Leo Zucker (57) ABSTRACT

A system for harvesting bone graft material for use during bone fusion surgery. In one embodiment, a bone cutting tool has a blade fixed on a distal end of a shaft. The distal end of the shaft is pivoted on a cage set between two bones to be fused, and the blade is activated to cut into the bones and form a solid bone segment in each bone as the tool shaft turns. A paddle is arranged to be inserted between the bones, and to displace the cut bone segments so that a leading portion of each segment enters the bone opposite the bone from which the segment was cut, a central portion of the segment spans across the bones, and a trailing portion of the segment remains in the bone from which it was cut. The displaced segments act as strut grafts to fuse the bones to one another.

2 Claims, 10 Drawing Sheets

(56) References Cited

U.S. PATENT DOCUMENTS

| | | |
|---|---|---|
| 8,628,534 B2 | 1/2014 | Jones et al. |
| 2006/0129243 A1 | 6/2006 | Wong et al. |
| 2006/0195106 A1 | 8/2006 | Jones et al. |
| 2006/0195107 A1* | 8/2006 | Jones ............... A61B 17/1624 606/79 |
| 2009/0054994 A1* | 2/2009 | Rogan ............... A61B 17/8805 623/23.72 |
| 2011/0035007 A1* | 2/2011 | Patel ............... A61F 2/4465 623/17.11 |
| 2011/0196373 A1* | 8/2011 | Jacob ............... A61B 17/1757 606/79 |
| 2012/0130380 A1 | 5/2012 | Babaev |
| 2012/0310350 A1 | 12/2012 | Farris et al. |
| 2013/0158668 A1 | 6/2013 | Nichols et al. |
| 2014/0163573 A1 | 6/2014 | Neubardt |

OTHER PUBLICATIONS

Biomet, Inc., C-Thru(tm) Anterior Spinal System, online advertisement (2014).
Biomet, Inc., Solitaire(tm)—C Anterior Spacer System, online advertisement (2014).

* cited by examiner

HARVESTING BONE GRAFT MATERIAL FOR USE IN SPINAL AND OTHER BONE FUSION SURGERIES

CROSS REFERENCE TO RELATED APPLICATION

This application is a continuation-in-part (CIP) and claims priority under 35 U.S.C. §120 of my co-pending U.S. patent application Ser. No. 14/524,044 filed on Oct. 27, 2014, and incorporated in its entirety by reference.

BACKGROUND OF THE INVENTION

Field of the Invention

The present invention relates to a system for harvesting bone graft material for use in bone fusion surgery, including but not limited to fusions of the spine.

Discussion of the Known Art

An object of spinal fusion surgery is to join vertebrae at an affected level of a patient's spine, by inducing the growth of bone tissue that is deposited between the vertebrae during surgery. When fully grown, the deposited bone tissue fuses the vertebrae solidly and permanently. The procedure is long known to reduce or eliminate severe back pain when, for example, an intervertebral disc is damaged or becomes ineffective. See, e.g., U.S. Pat. No. 9,042,960 (May 26, 2015), titled Determining and Placing Spinal Implants or Prostheses, which is incorporated herein by reference.

In a typical fusion procedure, the disc space between vertebrae is cleaned, and bone or a bone graft material is deposited in the space in a way that allows the material to grow and achieve a healthy fusion. Among available graft materials, bone graft harvested directly from the patient's own bone tissue (autograft) or from a donor, ceramics, bone morphogenic proteins, and/or stem cell based grafts, are frequently used. Of these, autograft obtained from the patient's iliac crest or pelvic area is known to work best to achieve a successful fusion.

Using the patient's own bone tissue as graft material works well to form a confluence of the material with the vertebral bones to be fused. It is also known that (a) the more autograft material used, the greater the likelihood of achieving a successful fusion, and (b) a solid piece of autograft material works better than smaller chips to promote fusion. Basic principles of orthopaedic surgery suggest that an optimum fusion results when a solid piece of bone is inserted to span the entire intervertebral disc space, and when opposite ends of the piece enter or penetrate the vertebral end plates facing the space.

U.S. Pat. No. 7,201,775 (Apr. 10, 2007), incorporated by reference, discloses a procedure that includes implanting a hollow cylindrical stabilizing device (see FIGS. 7 & 8 of the patent) between the end plates the vertebrae to be fused, and rotating the device so it gouges and shears off portions of the end plates which are then forced inside the device. The device has openings so that when oriented as in FIG. 11C of the patent, the sheared bone portions are exposed to the vertebrae through openings in the device in order to promote fusion. The procedure does involve a risk of crushing the end plates and thereby destroying the integrity of the remaining vertebral bone, however. That is, after the end plates are sheared by the device, one or both vertebrae may become prone to fracture and compress into the spinal canal. Also, the device does not work to translocate or displace a solid piece of bone from one vertebra so that an end of the piece enters the body of the other vertebra.

U.S. Pat. No. 8,328,870 (Dec. 11, 2012) describes an interbody fixation system including a cage having a number of blades mounted inside the cage. When the blades are turned not more than 45 degrees as shown in FIGS. 2 and 6C of the patent, the blades bite into the end plates of the opposed vertebrae and fix the position of the cage on and between the end plates. See also, U.S. Pat. No. 7,618,423 (Nov. 17, 2009) which relates to a system for performing spinal fusion including a graft holder assembly, a locking assembly, and a pair of bone graft implants that are introduced into a disc space to effect fusion; U.S. Pat. No. 8,353,912 (Jan. 15, 2013) disclosing an ultrasonic cleaning device for leveling the surfaces of vertebral end plates after the disc space between them is cleaned and before graft material is deposited in the space; and U.S. Pat. No. 8,343,178 (Jan. 1, 2013) describing an ultrasonic saw blade for cutting hard bone without damaging adjacent soft tissue. All relevant portions of the foregoing patents are incorporated by reference.

Notwithstanding known meticulous procedures for obtaining and using autograft material from a patient during surgery, there is no guarantee that a reliable and strong fusion will always be obtained, or that a so-called "non-union" will not occur. A need therefore exists for a system and procedure for obtaining autograft material from a patient during a bone fusion surgery, and for depositing the material between the bones to be fused so that (a) the material spans the space between the bones and also enters the bones, and (b) the material grows rapidly to obtain a healthy, strong, and permanent fusion of the bones.

SUMMARY OF THE INVENTION

According to the invention, a system for harvesting bone graft material for fusion surgery, includes a bone cutting tool having a tool shaft and a blade fixed at a distal end of the shaft. The tool is formed and dimensioned so that the shaft is insertable with the blade to a desired position in a space between two bones to be fused, and the blade cuts into the bones at the inserted position to form solid bone segments when the blade is activated and the shaft is turned.

A paddle or pusher is formed and dimensioned to be inserted at the desired position in the space between the bones so as to confront exposed surfaces of the bone segments cut by the blade, and to urge each segment to a position where a leading portion of the segment enters the bone opposite the bone from which the segment was cut, a central portion of the segment spans the space between the bones, and a trailing portion of the segment remains inside the bone from which it was cut. The segments thus act as strut grafts for fusing the bones to one another.

According to another aspect of the invention, a system for harvesting bone graft material for use in fusion surgery, includes a cage dimensioned and configured for insertion to a desired position in a space between two bones to be fused. The cage has a chamber that opens at top and bottom ends of the cage to face the bones, and the chamber has enough volume to contain a slurry of morselized bone and blood when effused by the bones.

An elongated cannula has an angled tip at a distal end, and the cage has a side wall with an opening for passing the cannula with the angled tip into the cage chamber. A flexible wire having a sharp tip is dimensioned for insertion through a passage in the cannula so that the wire tip projects beyond the angled tip of the cannula to contact confronting surfaces of the bones.

A drive mechanism is coupled to a proximal end of the cannula to rotate the cannula about its axis, so that the projecting wire tip cuts multiple grooves in the confronting bone surfaces as the cannula is moved axially in either direction. The cut bones effuse a slurry of morselized bone and blood that enters the cage chamber and fuses the bones to one another as the slurry heals.

According to a further aspect of the invention, a cage for insertion between two bones to be surgically fused, includes a front wall and a rear wall, and a bone graft cutting mechanism fixed inside the cage. The mechanism includes an outer shaft extending from a front wall of the cage toward the rear wall. A head of the outer shaft is configured to engage a mating tool for rotation of the outer shaft. A rear end of a sleeve is supported by the rear wall of the cage in alignment with the outer shaft, and a generally U-shaped bone cutting blade has a first leg joined to the outer shaft, and a second leg joined to the sleeve. An inner shaft extends inside the outer shaft and through the sleeve, and a front end of the inner shaft is accessible within the head of the outer shaft to engage a mating tool bit for rotation of the inner shaft.

A section of the inner shaft is exposed between an end of the outer shaft where the first leg of the blade is joined, and a front end of the sleeve where the second leg of the blade is joined. A paddle includes a pair of paddle arms that extend radially from either side of the exposed section of the inner shaft. The paddle arms are formed and arranged to displace solid bone segments that are formed inside the bones to be fused after the blade is rotated to cut into the bones, to positions at which the segments span and enter the bones to act as strut grafts.

For a better understanding of the invention, reference is made to the following description taken in conjunction with the accompanying drawing and the appended claims.

DETAILED DESCRIPTION OF THE INVENTION

The present invention resides in a system for harvesting graft material directly from a patient during a surgical bone fusion procedure. In the illustrated embodiment, the procedure is a spinal fusion wherein the bones to be fused are spinal vertebrae, and the harvested graft material spans the disc space between the vertebrae and also enters the vertebral bodies. As a result, the material grows quickly and obtains a healthy, solid, and permanent fusion. While the invention is illustrated and described herein in terms of a spinal fusion, persons skilled in the art will recognize that the invention can be applied to other fusion surgeries, for example, fusions of the ankle bones.

Figure 1:
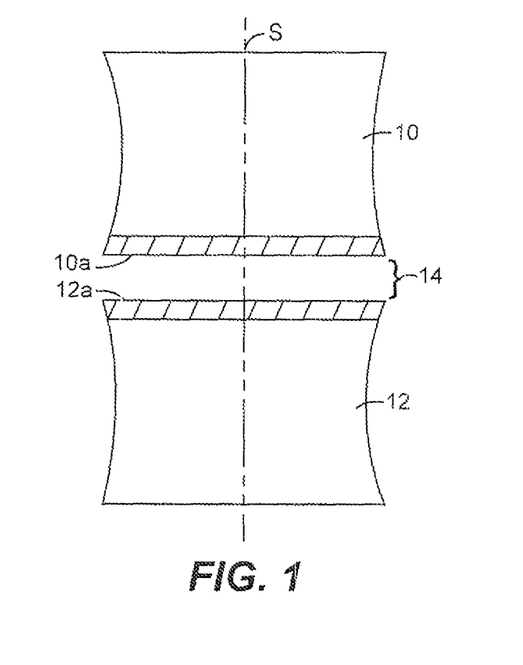
FIG. 1 illustrates two adjacent spinal vertebrae to be fused to one another, according to a first embodiment of the invention.

FIG. 1 is a diagram of two adjacent spinal vertebrae 10, 12. The spine has an axis S, and the vertebrae 10, 12 are separated by a disc space 14. End plates 10a, 12a on the vertebrae face one another across the disc space 14.

Figure 2:
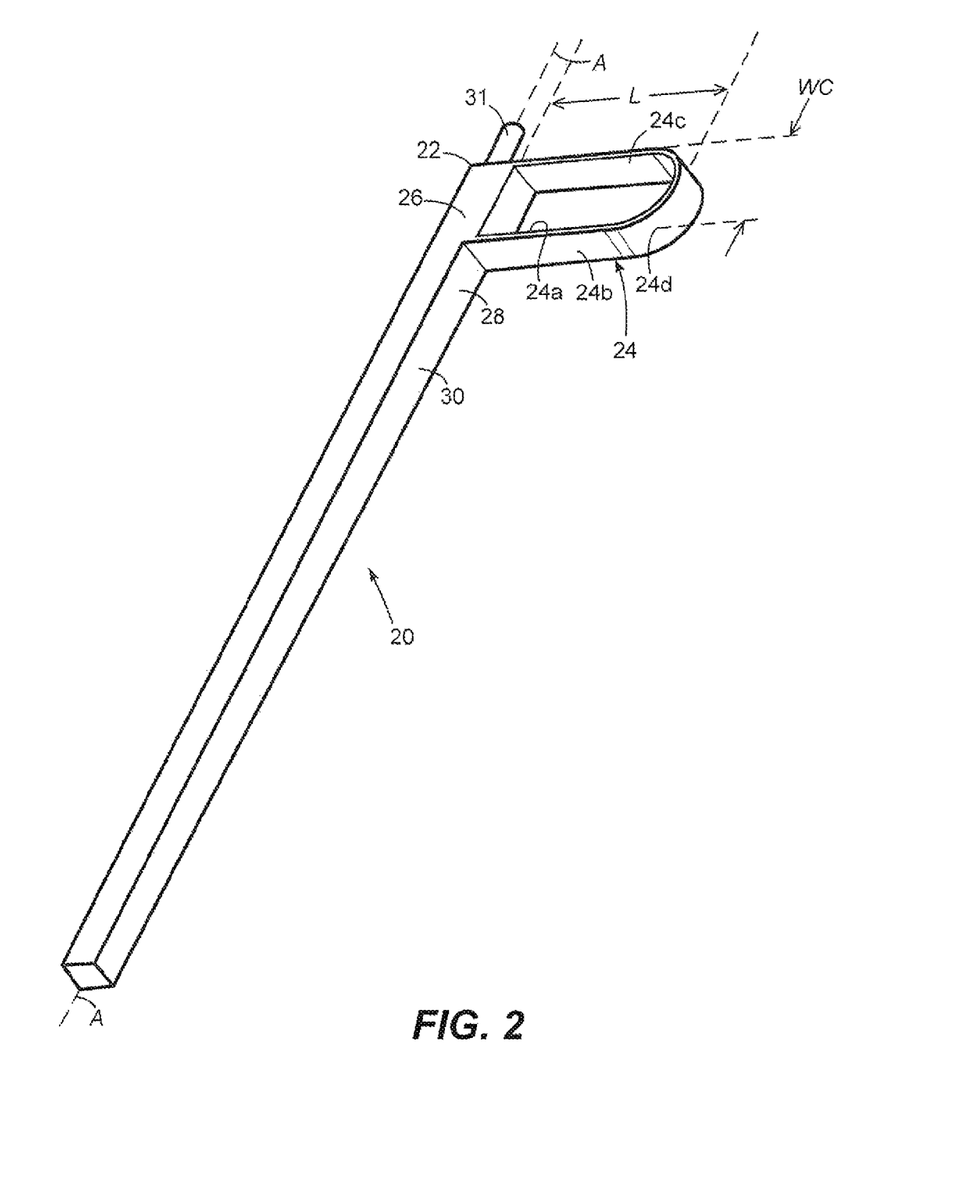
FIG. 2 shows a bone cutting tool having a shaft and a cutting blade at a distal end of the shaft, according to the invention.

In one embodiment of the invention, shown in FIGS. 2 to 9, a bone cutting tool 20 has a shaft 30 with a long axis A, and a generally U-shaped, ultrasonic cutting blade 24. The blade 24 has a base 26, and a cutting edge 24a formed along parallel legs 24b, 24c and a closed end 24d of the U shaped blade 24. As shown in FIG. 2, the blade legs 24b, 24c are spaced apart by width WC, and the closed end 24d of the blade extends by a length L from the base 26.

Figure 3:
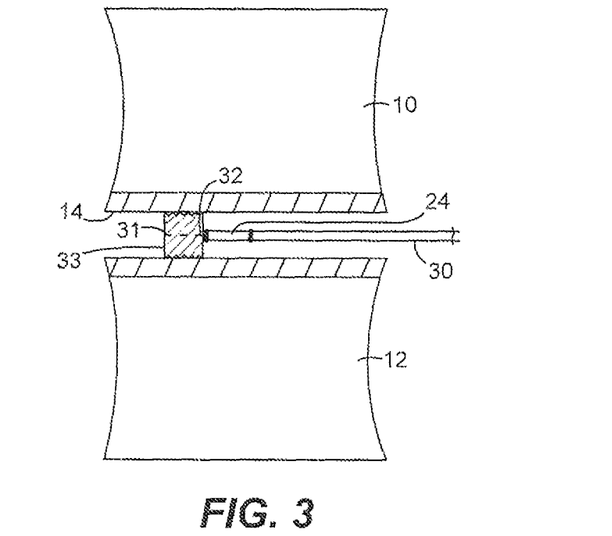
FIG. 3 shows the tool shaft in FIG. 2 inserted in a disc space between the vertebrae in FIG. 1, and a cage on which the shaft is pivoted to rotate with the blade.

The blade base 26 is formed by a distal end 28 of the tool shaft 30, and a pivot 31 projects axially from the distal end of the shaft. As seen in FIG. 3, the pivot 31 is received in a corresponding pivot opening 32 that is formed in a spacer or cage 33, once the cage 33 is fixed at a desired position in the disc space 14 between the vertebrae 10, 12. The cage 33 may be formed of a surgical metal, a polymer, a ceramic, or composites thereof. The pivot opening 32 in the cage 33 acts as an anchor point for the tool shaft 30 and any other instrumentation to be inserted in the disc space 14, while the cage 33 supports the vertebral bones 10, 12 above and below the disc space to prevent subsidence of bone graft segments to be obtained as described below. The cage 33 also serves to enhance the stability of the entire construct and thereby ensure a successful fusion.

If surgery is performed using a posterior approach, the cage 33 is inserted in the disc space 14 from the posterior side, and should be urged anteriorly as far as possible to lodge against the disc annulus as the vertebral bones 10, 12 compress the cage 33 from above and below. To provide an effective anchor point for the pivot 31 on the tool shaft 30, the cage 33 should be relatively large and curvilinear in shape to conform with the anterior disc space occupied by the cage. Cages typically have one or more apertures to allow bone graft material to be deposited inside them, and for the material to be exposed to and contact the vertebrae above and below the cage to allow the material to grow and bond the vertebrae 10, 12 solidly to one another.

Because, according to the invention, bone graft material is obtained directly from the vertebrae to be fused instead of from an outside source, it is therefore not necessary for the cage 33 to act primarily as a fusion device. Rather, the cage 33 can work mainly as a fixation device that joins to the vertebral bones 10, 12 above and below. An existing cage that also serves as a fixation device is available from Biomet, Inc., as the C-THRU™ Anterior Spinal System.

The above cage from Biomet has a large chamber that opens at the superior and inferior (top and bottom) ends of the cage, and inside of which graft material can be packed. Although as shown in FIG. 3 the cage 33 is not centered directly with respect to the end plates 10a, 12a of the vertebrae to be fused as described below, it may be desirable to use a cage similar to the one from Biomet that has a chamber which opens at both ends, and to form an opening in a side wall of the cage so that the blade 24 can be inserted by the tool shaft 30 into the cage chamber. In such a case, the cage 33 may be centered on the vertebral end plates 10a, 12a before the blade cuts into the end plates 10a, 12a, as described below. (See FIG. 11, and cage 100).

Figure 4:
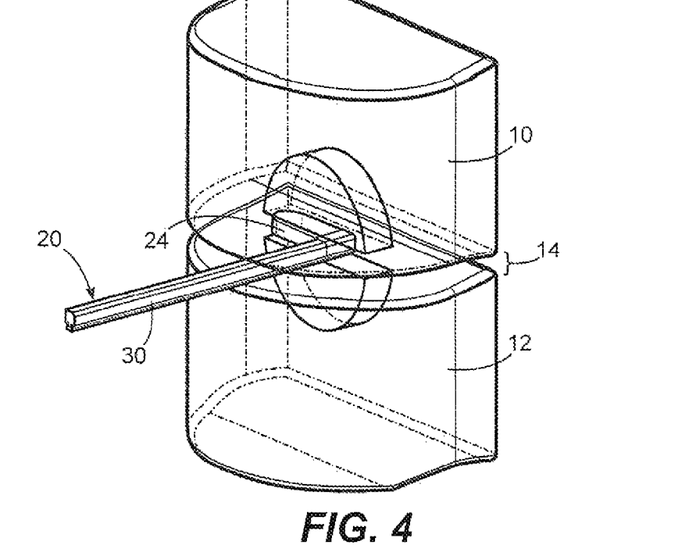
FIG. 4 is an enlarged, isometric view of the tool shaft and the blade inserted in the disc space as in FIG. 3.
Figure 5:
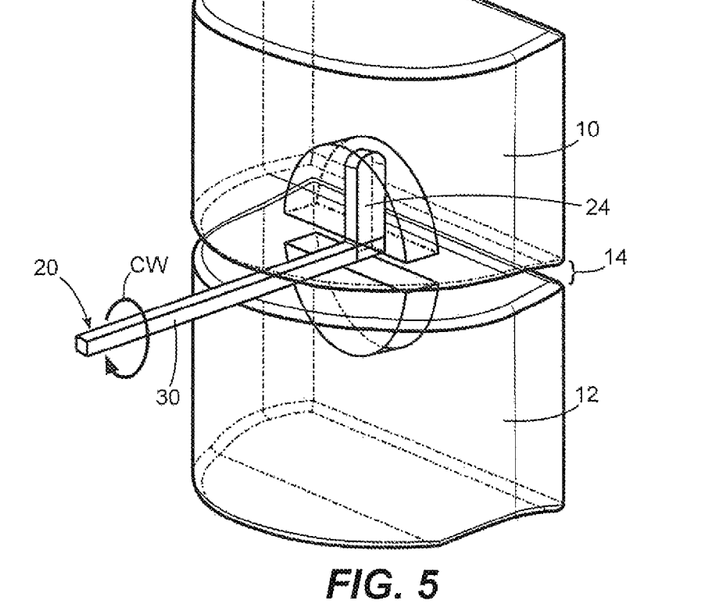
FIG. 5 is a view similar to FIG. 4, after the blade is turned 90 degrees from the position in FIG. 4 by the tool shaft.

As seen in FIG. 2, the U shaped blade 24 extends radially outward from its base 26 at the distal end 28 of the tool shaft 30. The legs 24b, 24c, and the closed end 24d of the blade 24 are in a plane that contains the shaft axis A. The bone cutting tool 20 with the blade 24 is dimensioned and formed so that the blade 24 can be inserted by the tool shaft 30 to a desired position in the disc space 14, with the plane of the blade 24 kept generally parallel to the end plates 10a, 12a of the vertebrae to be fused, as shown in FIG. 4. The cutting edge 24a along the blade 24 is activated, for example, by a conventional ultrasonic driver coupled in a known manner to the tool shaft 30. Ultrasonic bone cutting blades and methods of activating them are generally known, and persons skilled in the art will be able to construct and use the blade 24 as described herein. See, www.misonix.com.

Figure 6:
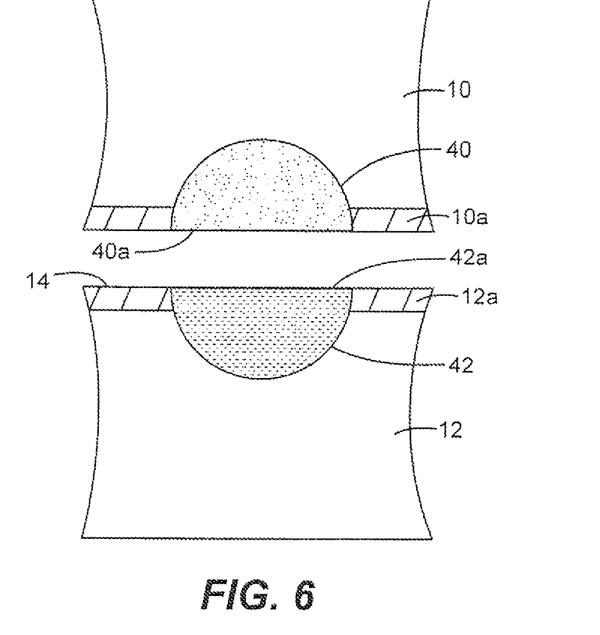
FIG. 6 illustrates two bone segments that are cut and formed inside the vertebrae by the tool blade.

The tool shaft 30 is rotated about its axis A by, e.g., a removable or cannulated handle having an axial thru passage keyed to the shaft cross section, or by a flexible motor drive, so that the blade's cutting edge 24a is urged a over a circular path through the vertebral end plates 10a, 12a, and adjacent regions inside the vertebrae 10, 12. See FIG. 5. As a result, and as illustrated in FIG. 6, the blade 24 forms two semi-circular solid bone segments 40, 42 in the vertebral bodies 10, 12 such that the radius of each segment 40, 42 corresponds to the radial length L of the blade 24, and the thickness of each segment corresponds to the spacing WC of the parallel blade legs 24b, 24c.

The bone segments 40, 42 are comprised of autologous graft material which, as explained below, will form strut grafts between the same vertebrae 10, 12 from which the segments were cut. Note in FIG. 6 that after the segments are cut by the blade 24, relatively flat surfaces 40a, 42a on the segments are exposed to face one another across the intervertebral disc space 14. While at this time the cutting blade 24 can be withdrawn from the disc space 14 together with the tool shaft 30, it may be desirable to leave the blade 24 and the shaft 30 in place, as noted below.

Figure 7:
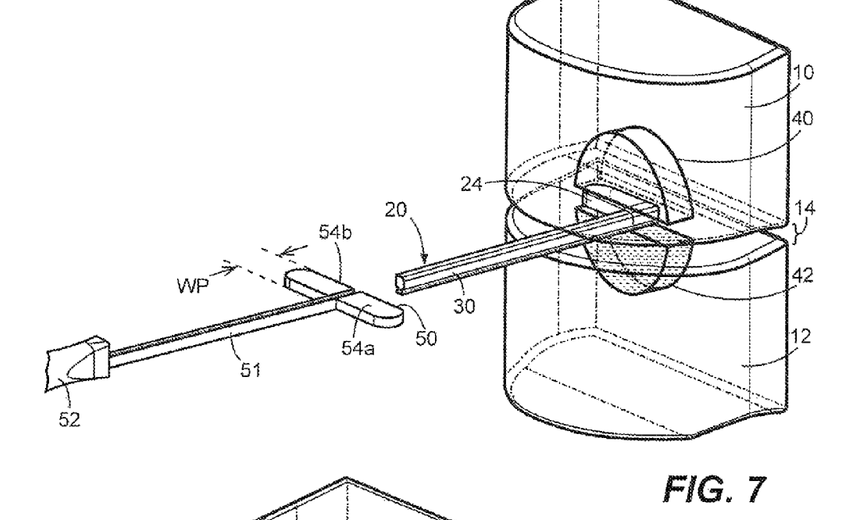
FIG. 7 is an isometric view of a pusher or paddle at a distal end of a shaft.
Figure 8:
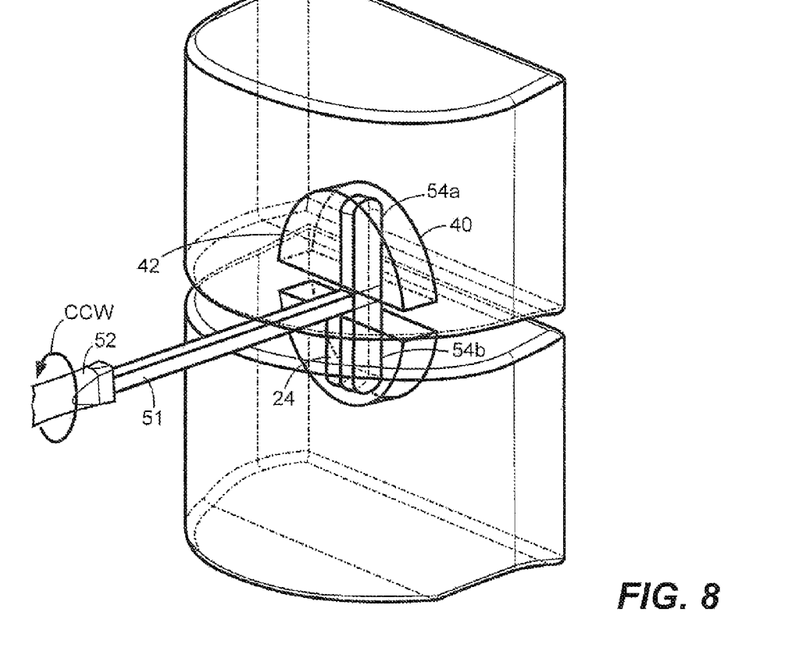
FIG. 8 is a view similar to FIG. 7, showing the paddle inserted in the disc space and after turning 90 degrees from the position in FIG. 7.
Figure 9:
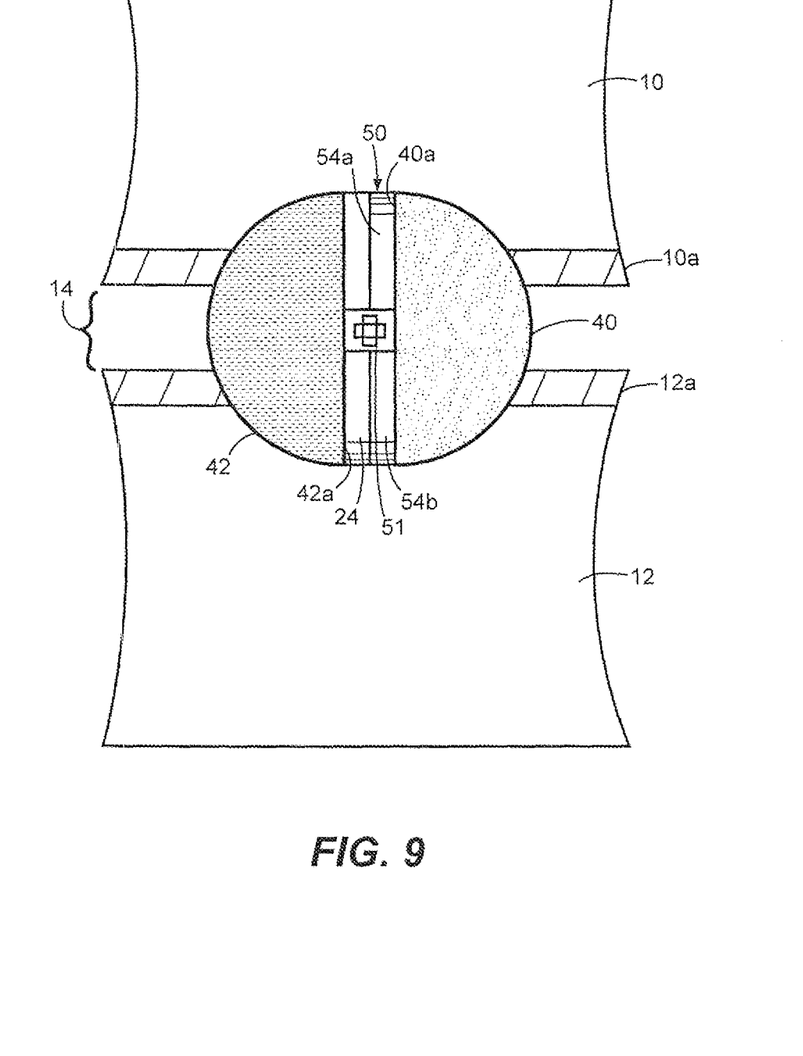
FIG. 9 shoes the bone segments in FIG. 6 acting as strut grafts between the vertebrae when the paddle is in the position in FIG. 8, according to the invention.
Figure 10:
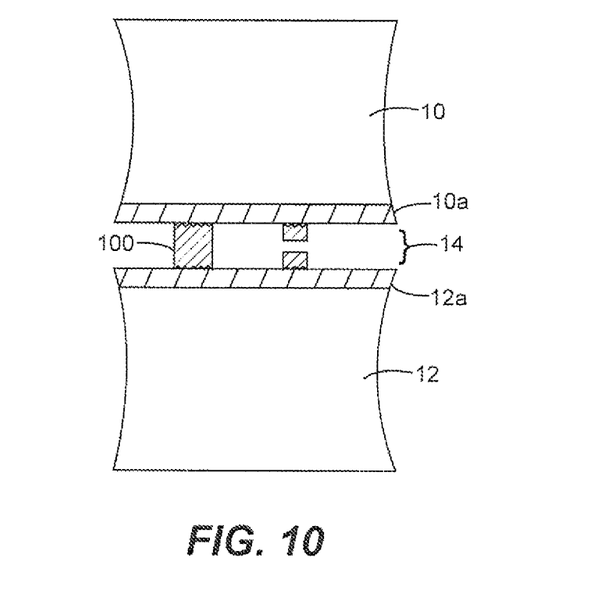
FIG. 10 shows the vertebrae in FIG. 1 before fusion and with a cage inserted in the disc space, according to a second embodiment of the invention.

After removing a handle or other drive from the tool shaft 30, and as shown in FIGS. 7 to 9, an elongated pusher or paddle 50 is inserted into the disc space 14 until the paddle 50 is aligned with the blade 24 and the exposed surfaces of the bone segments 40, 42. In the illustrated embodiment, the paddle 50 is fixed at a distal end of a cannulated shaft 51 having an axial passage keyed to the cross section of the tool shaft 30. The cannulated shaft 51 is slid onto the tool shaft 30, a handle 52 is provided on the proximal end of the shaft 51, and the paddle 50 is inserted via the shaft 51 into the disc space 14. Using the handle 52, the paddle 50 (together with the cutting blade 24 if left in place) is rotated about 90 degrees over the same circular path traversed by the blade 24 when forming the bone segments 40, 42, as described below.

If the cage 33 in FIG. 3 is of such size as to encompass areas of the vertebral end plates 10a, 12a to be cut by the blade 24, then both the blade 24 and paddle 50 should be able to be inserted inside the cage and to operate within the bounds of the cage. In such a case, the cage 33 may be formed with passages in its anterior and posterior facing side walls, so that the passages allow the cutting blade 24, paddle 50, and other required instrumentation to enter the cage from either direction depending on the approach taken by the surgeon.

In the illustrated embodiment, the paddle 50 has two U shaped arms 54a, 54b that extend radially from the shaft 51, and 180 degrees apart from one another. See FIGS. 7 to 9. Each paddle arm 54a, 54b has a width WP that does not exceed the width WC of the bone cutting blade 24. Likewise, the length of each paddle arm 50a, 50b does not exceed about one-half the length of either of the bone segment surfaces 40a or 42a facing the disc space 14. The entire paddle 50 may also be formed from one or more balloons which, when inflated, take the form of a rigid pusher or paddle device.

When the paddle 50 is inserted in the disc space 14, the paddle arms 54a, 54b are generally parallel to and overlie the surfaces 40a, 40b of the bone segments. The cannulated shaft 51 is turned about its axis A so that the paddle arms urge the bone segments 40, 42 confronting the arms to rotate partially out of the vertebra from which the segment was cut by, e.g., about 90 degrees as in FIG. 9. Accordingly, (i) a leading portion of each segment 40, 42 enters the vertebra opposite the vertebra from which the segment was cut, (ii) a central portion of each segment spans the disc space 14, and (iii) a trailing portion of each segment remains inside the vertebra from which it was cut.

When rotated as described above and shown in FIG. 9, each one of the bone segments 40, 42 forms a vertical strut graft that spans the disc space 14 fully and also penetrates both of the vertebrae 10, 12 to be fused. Each strut graft will therefore act as a pathway for bone growth and promote a healthy fusion of the two vertebrae. The tool shaft 30 may be withdrawn from the cage 33 inside the disc space 14, and the paddle 50 and the cutting blade 24 can remain in a vertical position sandwiched between the strut grafts formed by the bone segments with no adverse affect on the quality of the ensuing fusion.

After the blade 24 cuts into the vertebrae and the formed bone segments 40, 42 are rotated by the paddle 50, a massive release of blood will likely occur because the bone is very vascular. Accordingly, in addition to inserting and using a cage similar to the mentioned Biomet device in the disc space 14, a system should be in place to extinguish such hemorraging. One approach is to use a coagulating agent such as, for example, the Surgiflo® Hemostatic Matrix available from Ethicon US, LLC, and injecting the agent through an applicator tube into a port formed on the cage 33. Also, with much bleeding, there may be a need to seal the disc space 14 so the coagulating agent will stay inside the space. That is, the disc space 14 may need to be capped or sealed closed to confine the blood, the coagulating agent, and the graft bone segments inside the disc space. Once the coagulating agent is injected in the closed disc space, a pressurized environment is created and the bleeding should stop.

The cage may also have ports situated so that the coagulating agent produces a seal between the upper and the lower surfaces of the cage, and the adjacent vertebral bone. The seal should help to prevent bloody fluid from escaping above and below the cage through small gaps.

As the paddle 50 turns, and as described above, the paddle arms 54a, 54b are urged against the confronting surfaces 40a, 42a of the bone segments 40, 42 after the segments are cut and formed by the blade 24. The paddle 50 therefore does not occupy any space in which new bone graft will be deposited. Thus, as noted above, the paddle 50 can remain in the position in FIG. 9 with the graft bone segments 40, 42 at each side, and the vertebral bones 10, 12 above and below the paddle. Moreover, as the bones 10, 12 heal and the graft bone segments 40, 42 grow, the paddle 50 becomes firmly anchored inside the vertebrae 10, 12 and adds stability to the overall construct by pinning the vertebrae together. To that end, the paddle 50 may be constructed, for example, with extensible pins to engage the confronting surfaces 40a, 42a of the bone segments and/or the vertebrae 10, 12 above and below the paddle 50. Such engagement would stabilize the construct and ensure that the paddle 50 and the graft bone segments 40, 42 do not migrate. Together with the cage 33, the paddle 50 will also prevent subsidence from a collapse of the disc height.

It is also possible for the paddle 50 to be formed as a balloon so that, if desired after inflation and use, the paddle can be deflated and easily removed after being turned to the position in FIG. 9 along with the bone segments 40, 42 at either side. In such a scenario, any additional fixation that would otherwise result by using a more solid form of the paddle 50, would not be realized unless the balloons are later filled with a material such as, e.g., methyl methacrylate that would harden the balloons in place.

The paddle 50 may also be constructed in a known manner so that the paddle arms 54a, 54b overlie one another at one side of the cannulated shaft 51 as the paddle 50 is inserted in the disc space 14. Once positioned between the bone segments 40, 42, one of the paddle arms may then be displaced to the opposite side of the shaft 51 so that the paddle arms overlie the confronting surfaces 40a, 42a on both of the bone segments.

It may also be preferable to allow the solid bone cutting blade 24 to remain in situ, and no attempt made to withdraw it from between the bone segments 40, 42 once the bone segments are formed and the paddle 50 enters the disk space 14. This would help to ensure that the paddle arms 54a, 54b will follow the same path previously cut by the blade 24 when forming the bone segments. A deviation of even a millimeter to either side of the path might cause the paddle arms 54a, 54b to lock or jam against solid uncut vertebral bone and prevent the arms from urging the segments 40, 42 fully toward the position in FIG. 9. If the dimensional tolerances of the cage 33 allow enough precision with respect to positioning the cutting blade 24 and the paddle 50 during use, then it may be possible for the blade 24 to be withdrawn before the paddle 50 is inserted and the paddle arms are deployed.

The inventive system therefore has the following desirable features:

1. The bone cutting blade 24 can be activated ultrasonically to make the vertebral cuts safely and precisely;

2. The blade 24 and the paddle 50 can be made small enough to be inserted in the intervertebral disc space 14 during a minimally invasive surgical procedure; and 3. In addition to adding stability to the construct, the cage 33 provides a common fixed pivot point about which the cutting blade 24 and the paddle 50 can rotate, thereby ensuring that the bone segments 40, 42 will turn smoothly and accurately within the vertebrae 10, 12 when urged to do so by the paddle.

Another embodiment of the inventive system is illustrated in FIGS. 10 to 14. Instead of cutting and forming the solid graft bone segments 40, 42 and displacing them angularly as described above, a bone cutting instrument having a straight rather than a two-dimensional or U shaped cutting edge like the blade 24 is inserted in the disc space 14. The instrument is operated to strike the vertebral bones 10, 12 and groove them so that a slurry of morselized cortical and cancellous bone rich in osteogenic cells and blood oozes from the vertebrae. By confining the slurry inside the disc space 14, portions of the slurry also remain within the grooved portions of both vertebrae to produce a solid bony fusion.

A cage 100 is set in the disc space between the vertebrae 10, 12. See FIG. 10. The cage 100 may be similar to the earlier mentioned Biomet C-THRU Anterior Spinal System device, or equivalent. In addition, the cage 100 should have sufficient size and volume to contain and confine the slurry obtained from the vertebrae as detailed below, and be constructed so that its edges seal any gaps between the cage and either bone 10, 12. Such sealing prevents liquid graft material from migrating outside the internal chamber of the cage 100 and the intervertebral disc space. For example, a seal can be formed by constructing the cage 100 with internal and/or external channels that guide a sealing agent around the circumference of the superior and inferior edges of the cage 100, and the agent can be injected into the cage during the fusion procedure. The mentioned Surgiflo® Hemostatic Matrix is an example of such a sealing agent.

Figure 11:
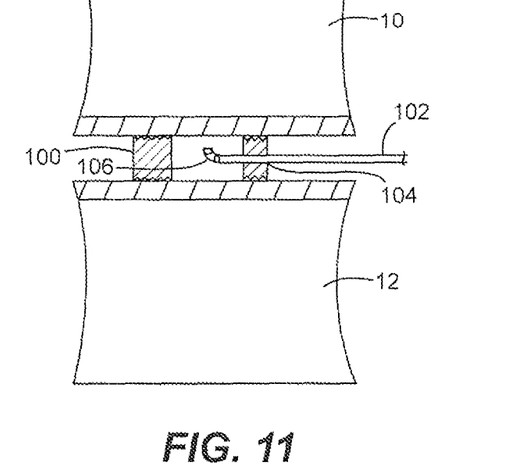
FIG. 11 shows a distal end of a cannula inserted in the disc space through an opening in a side wall of the cage in FIG. 10.
Figure 12:
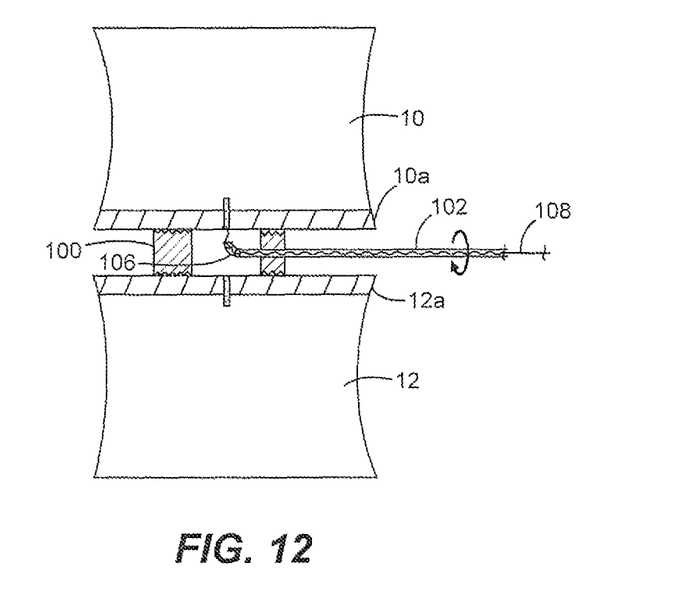
FIG. 12 shows a cutting tip of a flexible wire inserted through the cannula and into the disc space, with the wire tip angled toward one of the vertebrae.
Figure 13:
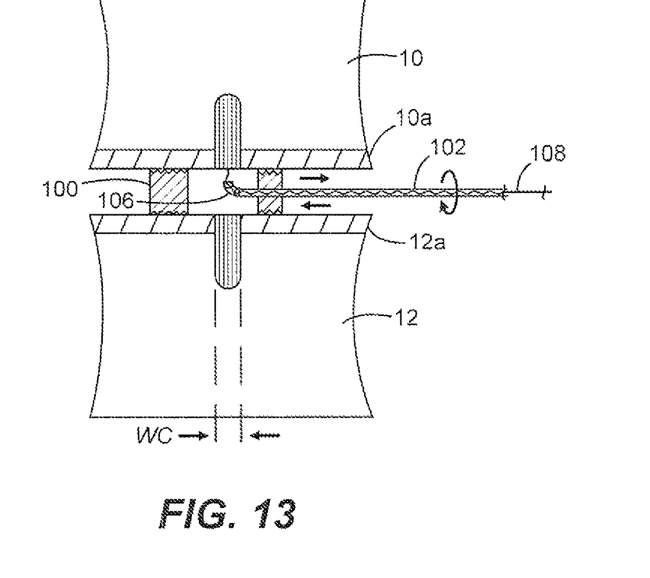
FIG. 13 shows the tip of the wire cutting multiple grooves in the vertebrae to be fused.

As seen in FIGS. 11 to 13, a cannula 102 is inserted through an opening 104 in the wall of the cage 100, and the cannula 102 has a distal tip 106 that is angled to be directed toward the vertebrae above and below the perimeter of the cage when the cannula 102 is rotated about its axis. A flexible, sharp tipped wire 108 is inserted through the cannula 102, past the distal tip 106 of the cannula, and against the end plate 10a or 12a of a confronting vertebra. A motor or other drive mechanism is coupled to a proximal end of the cannula 102, and spins the cannula over multiple revolutions so that the tip of the wire 108 cuts into the end plates 10a, 12a of both vertebrae.

The wire 108 is urged farther into the cannula 102 so that the wire tip cuts a groove completely through the end plates and adjacent regions of the vertebrae 10, 12, as seen in FIG. 12. The position of the wire 108 at the tip 106 of the cannula is adjusted and the cannula 102 is moved axially in anterior and posterior directions so that the combined width WC of all the vertebral cuts is increased as desired. See FIG. 13. The cannula 102 and wire 108 are then withdrawn from inside the cage 100 and the disc space.

Figure 14:
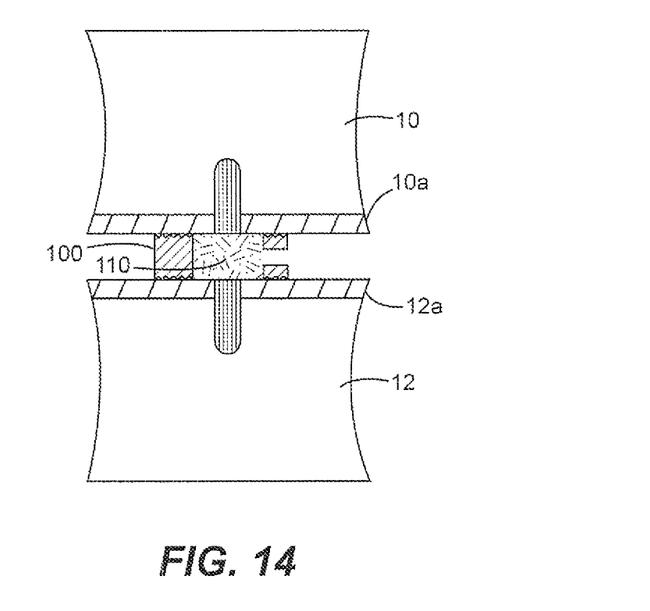
FIG. 14 depicts the effusion of a bony slurry from the cut vertebrae, and the confinement of the slurry in the cage, according to the invention.

As a result and as shown in FIG. 14, all of the bony slurry 110 obtained from the cut vertebrae is contained either inside the cage 100 in the disc space, or within the vertebrae 10, 12 in the region of the grooved cuts. Upon healing, the slurry forms a solid bony fusion of the vertebrae. If needed, a second cage or other device can be provided to cap or otherwise seal the cage 100 and the disc space to ensure the slurry stays so confined before healing.

Figure 15:
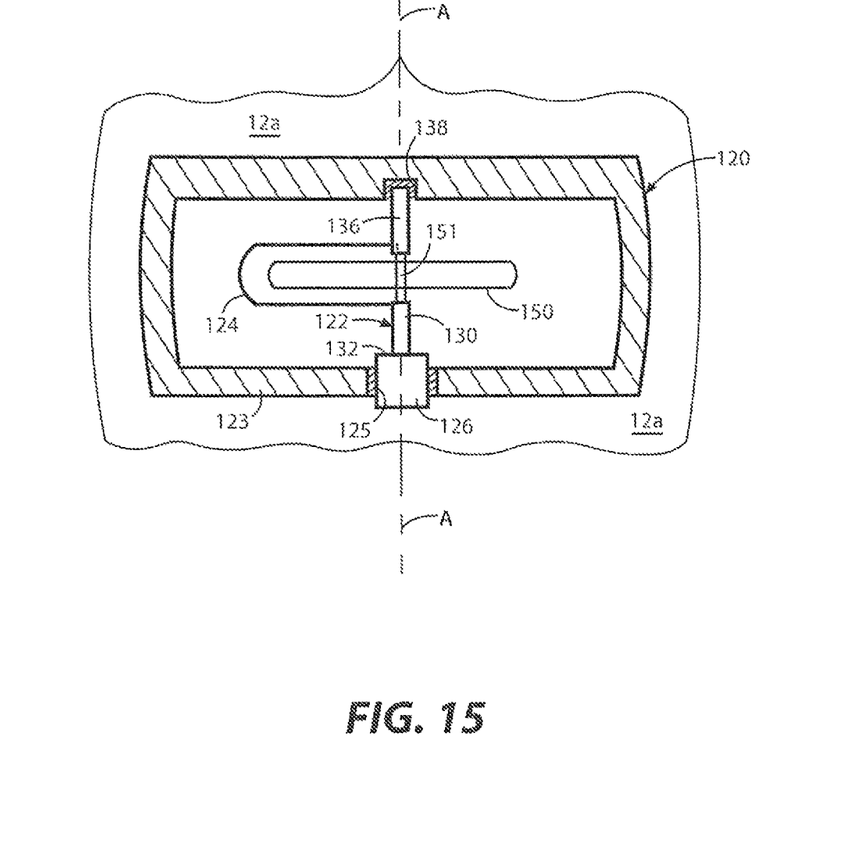
FIG. 15 shows the interior of a cage including a bone cutting blade and paddle mechanism fixed inside the cage, according to the invention.
Figure 16:
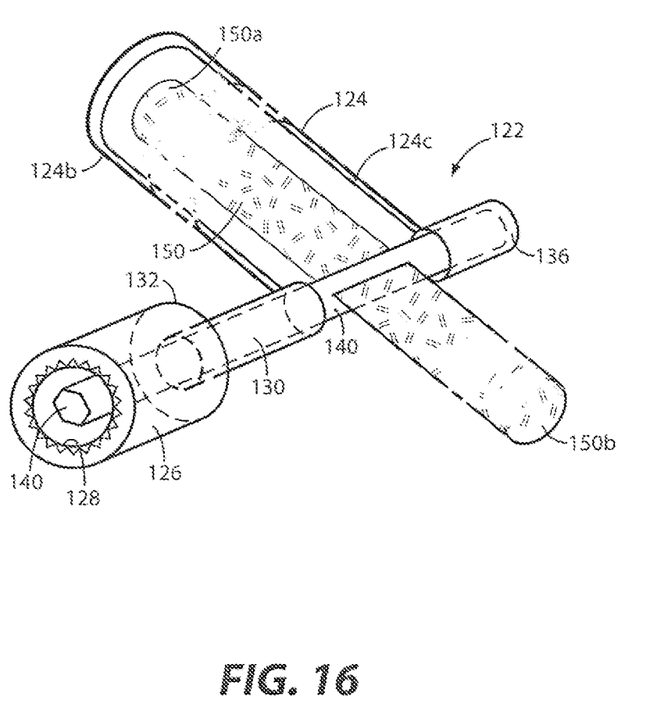
FIG. 16 is an enlarged, isometric view of the blade and paddle mechanism in FIG. 15.

FIG. 15 is a plan view of the interior of a cage 120 having a built-in blade and paddle mechanism 122 constructed and arranged to be operated from outside the cage 120, according to a further embodiment of the invention. FIG. 16 is an enlarged, isometric view of the blade and paddle mechanism 122.

The cage 120 may be formed, for example, from a surgically approved metal or metal alloy, or a strong plastics such as polyether ether ketone (PEEK). The side walls of the cage 120 as viewed in FIG. 15 are preferably as thin as possible while still having enough strength to prevent the cage 120 from deforming after the cage is inserted and fixed between spinal vertebrae or other bones to be fused.

A front wall 123 of the cage 120 in FIG. 15 has an opening 125 in which a head 126 of a first shaft 130 and a front end of a second shaft 140 (see FIG. 16), can each be accessed by a corresponding tool to rotate the associated shaft. That is, the shafts 130, 140 can be rotated independently of one another as desired by a mating tool from outside the cage 120. In the disclosed embodiment, the first shaft 130 is hollow, and the second shaft 140 extends coaxially inside the first shaft 130.

As shown in FIG. 16, the head 126 of the first (or outer) shaft 130 is, for example, in the form of a cylindrical socket having a series of teeth or grooves formed about its inner circumference for engaging a mating tool bit. The outer shaft 130 extends axially a certain distance from a rear wall 132 of head 126 toward a back wall of the cage 120, and a first leg 124b of a generally U-shaped bone cutting blade 124, which may be similar to the blade 24 in FIG. 2, is joined at one end of the leg 124b to the shaft 130. The second leg 124c of the blade 124 is joined to a front end of a sleeve 136 that is aligned axially with the outer shaft 130, and a rear end of the sleeve 136 is seated in the rear wall of the cage 120 at 138 (FIG. 15) for smooth rotation about the sleeve axis.

The second (or inner) shaft 140 of the blade and paddle mechanism 122 extends axially inside the outer shaft 130, and through the sleeve 136 toward the rear of the cage 120. The front end of the inner shaft 140 is keyed and is accessible within the cylindrical head 126 of the outer shaft 130 so that the front end of the shaft can be engaged for rotation by a mating tool bit. A section of the inner shaft 140 is exposed between the end of the outer shaft 130 to which the blade leg 124b is joined, and the front end of the sleeve 136 where the blade leg 124c is joined.

A paddle 150 has a pair of arms 150a, 150b that extend radially from either side of the exposed section of the inner shaft 140, and the arms are spaced 180 degrees apart from one another. The paddle arms 150a, 150b are formed and arranged to displace solid bone segments that are formed inside the bones to be fused after the blade 124 is rotated to cut into the bones, to positions at which the bone segments span and enter the bones to form strut grafts. The axial width and the radial length of the paddle arms 150a, 150b are such that when the U-shaped blade 124 is rotated by the outer shaft 130 over one full revolution while the paddle arms remain stationary, the blade 124 clears the perimeters of the paddle arms by at least 1 mm, and preferably by not more than 5 mm.

In use, and as in the first embodiment of the present invention, the blade 124 is activated and rotated 360 degrees by the outer shaft 130 so as to cut into the bones above and below the cage 120 and thus form two semicircular solid bone segments. After the segments are formed, the paddle arms 150a, 150b are displaced angularly about 90 degrees by the inner shaft 140. Each bone segment is thereby urged by a confronting paddle arm to rotate until (i) a leading portion of the segment enters the opposed bone, (ii) a central portion of the segment spans the space in which the cage 120 is fixed between the bones, and (iii) a trailing portion of the segment remains in the bone in which it was formed.

While the foregoing represents preferred embodiments of the invention, it will be understood by those skilled in the art that various modifications, adaptations, and additions may be made without departing from the spirit and scope of the invention.

For example, while the invention is described herein as applied to a spinal fusion, the invention may be adapted for other bone fusion procedures as well, for example, fusions of the ankle bones. Further, although a particular configuration is disclosed herein to enable the blade and the paddle shafts 130, 140 each to be rotated as desired from outside the cage 120, other equivalent configurations for rotating the blade 124 and the paddle 150 inside the cage may also be used. See, e.g., U.S. Pat. No. 7,972,364 (Jul. 5, 2011) which is incorporated by reference.

Accordingly, the invention includes all such modifications, adaptations, and additions as are within the scope of the following claims.

I claim:

1. A system for harvesting bone graft material for use during a surgical fusion procedure, comprising:

a bone cutting tool including an elongated tool shaft extending from a proximal end to a distal end along a longitudinal axis, and a generally U-shaped blade extending radially outward from the distal end of the shaft, the blade having a base formed by a distal portion of the elongated tool shaft at the distal end of the shaft, a pair of parallel legs projecting radially outward from the distal portion of the shaft and an arcuate end portion connected to the parallel legs and forming a concave surface facing said distal portion, wherein the parallel legs, the arcuate end portion and the distal portion forming the base are in a plane that contains the longitudinal axis of the elongated tool shaft, and a cutting edge is formed along the legs and the arcuate end portion of the U-shaped blade, so that a through opening extends through the U-shaped blade which opening is enclosed by the base, the legs, and the arcuate end portion of the blade;

a cage having opposite surfaces and configured to be inserted and fixed in a space between two bones to be fused to one another, such that each of the opposite surfaces is configured to engage a corresponding one of the two bone, wherein the cage is configured to support the two bones above and below the space and to maintain fusion of the two bones relative to one another, the cage having a pivot opening formed in a wall of the cage extending between the opposite surfaces;

the tool shaft of the bone cutting tool has a pivot extending axially along the longitudinal axis from the distal end of the shaft, wherein the pivot is received in the pivot opening in the wall of the cage when the distal end of the tool shaft including the U-shaped blade is inserted in the space between the two bones, and the cutting edge of the blade is configured to rotate about the longitudinal axis when the pivot is received in the pivot opening, and to cut into each of the two bones and form a generally semicircular solid bone segment in each of the two bones when the tool shaft is rotated about its longitudinal axis; and elongated paddles in the form of a pair of U-shaped arms extending radially outward from a distal end of a cannulated paddle shaft approximately 180 degrees apart from one another, so that the paddles are insertable via the cannulated paddle shaft in the space between the bones by passing the elongated tool shaft of the bone cutting blade through an axial passage in the cannulated paddle shaft in a keyed configuration, and the paddles are dimensioned and configured to align with and overlie exposed surfaces of the bone segments formed by the bone cutting blade so that when the paddle shaft is rotated about the longitudinal axis, the paddles are operative to displace the blade and each of the bone segments to a position where (i) a leading portion of the segment enters the bone opposite the bone from which the segment was cut, (ii) a central portion of the segment spans the space between the bones, and (iii) a trailing portion of the segment stays inside the bone from which it was cut, so that the displaced bone segments act as strut grafts to fuse the two bones to one another.

2. A system for harvesting bone graft material according to claim 1, including an ultrasonic driver coupled to the shaft of the bone cutting tool for energizing the blade of the tool.

\* \* \* \* \*